United States Patent
Prescott et al.

(10) Patent No.: US 8,961,603 B2
(45) Date of Patent: Feb. 24, 2015

(54) SUCTION GRASPER FOR OSSICULAR PROSTHESIS

(75) Inventors: Anthony D. Prescott, Arlington, TN (US); Murray Beard, Cordova, TN (US)

(73) Assignee: Enteroptyx, Memphis, TN (US)

( * ) Notice: Subject to any disclaimer, the term of this patent is extended or adjusted under 35 U.S.C. 154(b) by 310 days.

(21) Appl. No.: 13/528,242

(22) Filed: Jun. 20, 2012

(65) Prior Publication Data

US 2013/0345809 A1 Dec. 26, 2013

(51) Int. Cl.
*A61F 2/18* (2006.01)

(52) U.S. Cl.
USPC .......................................................... 623/10

(58) Field of Classification Search
USPC .......................................................... 623/10
See application file for complete search history.

(56) References Cited

U.S. PATENT DOCUMENTS

| | | | |
|---|---|---|---|
| 4,281,419 A | 8/1981 | Treace | |
| 4,473,073 A | 9/1984 | Darnell | |
| 5,171,240 A | 12/1992 | Hanwong | |
| 5,178,623 A | 1/1993 | Cinberg et al. | |
| 5,354,298 A | 10/1994 | Lee et al. | |
| 5,361,760 A | 11/1994 | Normann et al. | |
| 5,466,239 A | 11/1995 | Cinberg et al. | |
| 5,827,295 A | 10/1998 | Del Rio et al. | |
| 5,947,974 A | 9/1999 | Brady et al. | |
| 5,993,459 A | 11/1999 | Larsen et al. | |
| 6,245,077 B1 | 6/2001 | East et al. | |
| 6,626,913 B1 | 9/2003 | McKinnon et al. | |
| 6,689,146 B1 | 2/2004 | Himes | |
| 7,553,328 B2 | 6/2009 | Steinhardt et al. | |
| 2004/0249458 A1 | 12/2004 | Kahana et al. | |
| 2005/0228394 A1 | 10/2005 | Bihary et al. | |
| 2007/0083263 A1 | 4/2007 | Steinhardt et al. | |
| 2007/0162119 A1* | 7/2007 | Johnson | 623/10 |
| 2009/0105749 A1 | 4/2009 | deJuan et al. | |
| 2009/0209972 A1* | 8/2009 | Loushin et al. | 606/109 |
| 2010/0142739 A1 | 6/2010 | Schindler | |
| 2010/0174292 A1 | 7/2010 | Labadie et al. | |
| 2010/0191331 A1 | 7/2010 | Steinhardt et al. | |
| 2013/0231529 A1* | 9/2013 | John et al. | 600/104 |
| 2013/0345722 A1* | 12/2013 | Margulis | 606/131 |
| 2014/0031852 A1* | 1/2014 | Edgren et al. | 606/199 |

OTHER PUBLICATIONS

Disposable Suction Tubes, Product descriptions, available at http://www.spiggle-theis.com/en/products/disposable-suction-tubes, 2011.
Otology, GYRUS ACMI, Explorent Surgical Instruments, 2007.
Otology Instruments, Selected pages from Spiggle & Theis Medizintechnik, Product Descriptions, 2009.

* cited by examiner

*Primary Examiner* — Suzette J Gherbi
(74) *Attorney, Agent, or Firm* — Gordon & Jacobson, PC (57) ABSTRACT

A suction activated instrumentation system for use in implanting an ossicular prosthesis into the middle ear includes a suction handpiece and a vacuum source. A removable suction tip is coupled to the handpiece for engaging an ossicular prosthesis. The suction tip includes a distal portion with an elongate slot opening at an end face, and two arms defined at the end face. When suction is applied through the suction tip, the prosthesis is drawn against the end face and retained between the arms. In the event the prosthesis is inadvertently contacted during implantation, the suction tip provides for self-correction, causing a prosthesis to re-orient into the prior intended configuration.

17 Claims, 5 Drawing Sheets

SUCTION GRASPER FOR OSSICULAR PROSTHESIS

BACKGROUND OF THE INVENTION

1. Field of the Invention

The present invention relates to surgery. More particularly, the invention relates to surgical instruments used in performing surgery in the middle ear, and specifically for handling ossicular prostheses implantable in the middle ear.

2. State of the Art

Hearing is facilitated by the tympanic membrane transforming sound in the form of acoustic sound waves within the outer ear into mechanical vibrations through the chain of ossicles (malleus, incus, stapes) in the middle ear. These vibrations are transmitted through the ossicles to the lower footplate of the stapes where micro or macro motion of the footplate results in compression waves within the fluid of the inner ear. These compression waves lead to vibrations of the cilia (hair cells) located within the cochlea where they are translated into nerve impulses. The nerve impulses are sent to the brain via the cochlear nerve and are interpreted by the brain as sound.

Hearing efficiency can be lost to erosion of the ossicular bones. Various combinations or portions of the bones can be replaced. For example, all of the ossicles between the tympanic membrane and the stapes footplates can be replaced using a total ossicular replacement prosthesis, or TORP. A TORP includes a proximal disc-like head in contact with the tympanic membrane, a longitudinal shaft, and a shoe at a distal end for contacting the footplate of the stapes, and distributing the force from the head end at the tympanic membrane to the shoe at the distal end positioned on the footplate. Alternatively, the malleus and incus can be replaced leaving all or a portion of the stapes intact. The prosthesis for such a procedure is a partial ossicular replacement prosthesis, or PORP. A PORP also includes a head for placement at the tympanic membrane and includes bell or cup that seats over the capitulum and/or junction of the crura of the stapes. As yet another alternative, the stapes can be replaced, leaving the malleus and incus substantially intact. The determination of which one or more ossicles is to be replaced with a prosthesis is determined based on the cause of the hearing loss, the quality of the ossicles, and the judgment of the surgeon.

Regardless of which prosthesis is determined to be appropriate and selected for implantation, the prosthesis is extremely small. Typically, dimensions for the prosthesis range from 3 to 7 mm in length and a shaft diameter of less than 1 mm. The surgeon uses a tool to engage and manipulate the prosthesis into position within the middle ear structure. Known tools include a mechanical grasper and a suction tip to place and position ossicular prostheses. These tools are elongate, with a distal implant manipulating end of the instrument significantly displaced from the proximal hand-holdable portion. This amplifies motion from the surgeon's handle to the distal end, where steadiness is desirable.

When using a mechanical grasper, in order to release the prosthesis, a force is applied at the proximal handle end to move parts of the grasper relative to each other, which is then amplified as movement at the distal end. This amplified and often uncontrolled movement, can result in displacement of the prosthesis. Also, if a prosthesis held by a mechanical device is inadvertently contacted during insertion, it can be damaged if held too tightly by the device, or can be dropped or displaced out of intended orientation; it is very difficult to reengage or reorient the prosthesis once displaced from its position in the grasper once the distal end of the grasper is located within the middle ear.

Instruments that use suction to hold a prosthesis have the advantage in that mechanical forces are not required at the proximal end of the device to release the implant; thus, such forces cannot be amplified to displace the prosthesis from the intended target and release of the prosthesis should be more precise. However, current suction instruments do not have the ability to maintain implant position and/or re-orient a prosthesis in the event the prosthesis is inadvertently displaced from its initial position. If the prosthesis is off-position, approaching the anatomy for implantation may be difficult or impossible.

SUMMARY OF THE INVENTION

In accord with the invention, a suction grasper instrument for grasping an ossicular prosthesis is provided. The instrument includes a reusable handpiece and a disposable prosthesis-adapted suction tip. The prosthesis-adapted suction tip has a distal end that is adapted in geometry to the proximal end of the ossicular prosthesis.

In accord with one aspect of the invention, the prosthesis-adapted suction tip is adapted for use with a stapedial prosthesis that replaces the stapes between the incus and the stapes footplate. The stapedial prosthesis has a wire-form loop or crook extending in a plane formed with a wire of a certain diameter. The loop has a loop diameter defining a center and is sized to stably engage about the incus.

The prosthesis-adapted suction tip for the stapedial prosthesis has a longitudinal axis, an internal bore or passageway, and a flattened distal portion with an end face. The end face is either perpendicular to the longitudinal axis or provided at an oblique axis thereto. A non-circular slot opening is defined at the distal end of the distal portion in fluid communication with the internal bore and applied through the handpiece. The slot opening has a longer length and a shorter width, with the width preferably slightly larger than the diameter of the wire-form, and the length adapted to receive therein a small portion of the loop. A notch extends across the length of the slot opening at the distal end of the suction tip to define two short arms. The notch is preferably at a depth less than the diameter of the wire-form.

In use, suction is applied through the handpiece and prosthesis-adapted suction tip. As the distal end of the suction tip is brought toward the loop of the prosthesis, the suction draws the loop slightly inside the slot opening. When the loop is drawn into the slot opening, the length of the slot opening is parallel to the plane of the loop. Air is drawn into the slot around the wire and stabilizes the prosthesis at the distal end of the suction tip. In addition, the two short arms extend about the loop and provide stability to the orientation of the loop and thus the prosthesis. Once the prosthesis is engaged in an orientation, the suction tip can be rotated on the handpiece to change its orientation about its longitudinal axis. In the event the prosthesis is contacted during implantation, the suction tip is adapted to re-orient the prosthesis into the intended orientation, drawing the loop of the prosthesis back into the slot opening prosthesis and with the notch arms righting the prosthesis into axial alignment with the tube adapter. In addition, the prosthesis can rotate about a center of the loop for correct positioning during placement. The end face of the suction tip can be obliquely oriented to facilitate delivery of the prosthesis to the incus.

In another configuration of a prosthesis-adapted suction tip, the suction tip is structurally adapted for grasping a total or partial ossicular prosthesis (TORP or PORP). The TORP or PORP head has a disc-like configuration with a radially extending flat spoke having a length and a width.

The suction tip for the TORP or PORP has a longitudinal axis, and an end face. The end face is either perpendicular to the longitudinal axis or provided at an oblique axis thereto. A non-circular slot opening is defined at the end face. The slot opening has a longer length and a shorter width, with the length approximating but preferably slightly larger than the width of the spoke of the head of the prosthesis. The distal portion of the tube defines two extending arms, one on either end of the elongate slot between which the spoke of the prosthesis head can be stably received.

In use, suction is applied through the handpiece and suction tip. As the distal end of the suction tip is then brought toward the spoke of the head of the prosthesis, the suction draws the spoke against the distal face. With air being drawn around the outside of the spoke at the outer ends of the elongate slot. The angle of the end face allows the prosthesis to be oriented relative to the longitudinal axis to provide an approach angle into the middle ear that facilitates implantation. The prosthesis adapted suction tip can be rotated on the handpiece to change its rotational orientation about its longitudinal axis. In the event the prosthesis is contacted during implantation, the suction tip is adapted to re-orient the prosthesis into the intended orientation, drawing the spoke of the head of the prosthesis back between the arms, against the slot opening, and into the desired alignment.

In either configuration, the prosthesis may be released without mechanical activation. Once the prosthesis is placed at its intended location, suction is deactivated and the prosthesis is released from the suction tip.

The suction tip is easier to manufacture than mechanical graspers, is significantly less expensive to manufacture than mechanically operated graspers, and provides more stability and control than any existing instruments for manipulating an ossicular prosthesis for accurate implantation. In addition, the suction tip provides for self-orientation and self-correction, causing the prosthesis to re-orient into the prior intended configuration in the event the prosthesis is unintentionally dislodged from its initial configuration.

DETAILED DESCRIPTION OF THE PREFERRED EMBODIMENTS

Figure 1:
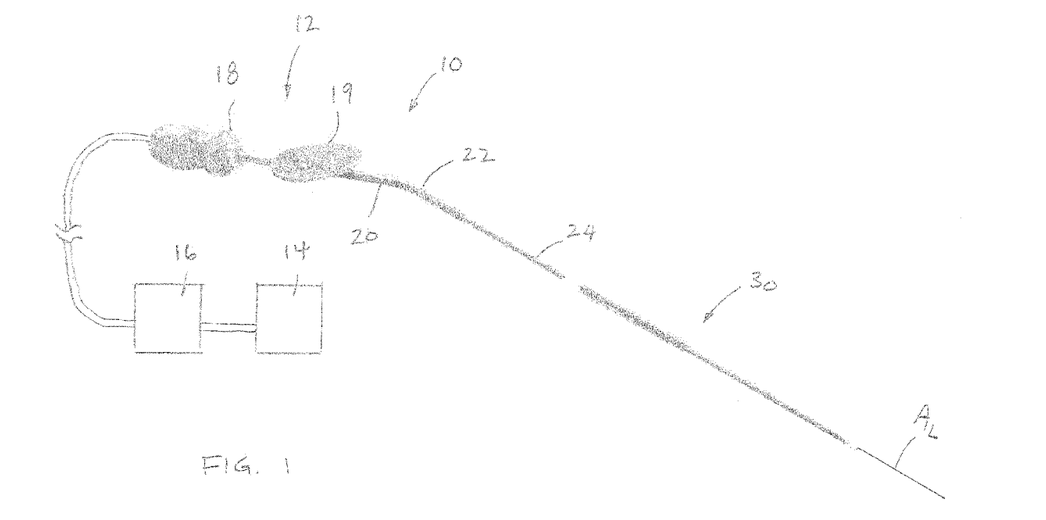
FIG. 1 is a perspective exploded view of a suction system including a suction handpiece and a prosthesis-adapted suction tip according to the invention.

Referring now to FIG. 1, a suction system 10 for use in implanting an ossicular prosthesis into the middle ear is shown. The suction system 10 includes a suction handpiece 12, a vacuum source 14 connected to the handpiece, and an optional footswitch 16 for turning on and off power at the vacuum source or interrupting application of suction from the vacuum source 14 to the handpiece 12. The handpiece 12 includes a handle portion 18 adapted for stable positioning and grasping in a hand of a surgeon, a thumb plate 19 with suction bypass hole, and a tubular shaft 20. The tubular shaft 20 includes a relatively proximally defined angle or bend 22 that provides ergonomics to the system during use and facilitates manipulation of a grasped prosthesis, as described below, without interrupting viewing of the surgical site. The shaft 20 also includes a reduced diameter distal coupling portion 24.

A prosthesis-adapted suction tip 30 is coupled to the coupling portion 24 of the handpiece 12. The suction tip 30 is an elongate tubular member preferably made of a plastic, but optionally metal. The tube 30 has a longitudinal axis $A_L$, a passageway 32 extending along the axis, a proximal portion 34, and a distal portion 36. The proximal portion 34 is sized to fit over the coupling portion 24, preferably with a slight friction fit engagement. Alternatively, the suction tip 30 and coupling portion 24 may be coupled in another manner that allows the suction tip to be coupled to the coupling portion in a preset rotational orientation, such as a threaded engagement. The suction tip 30 and coupling portion 24 may also be coupled with a luer connector or bayonet lock to ensure a degree of longitudinal stabilization between the components. If the coupling between the adapter and coupling portion is locked (e.g., threaded, luer, bayonet), the suction tip may be rotatable relative to its proximal coupling to allow rotation of the tube adapter during use without compromising the coupling between the suction tip and the coupling portion. As yet another alternative, the handpiece may include an opening in which the suction tip is received to couple the suction tip to the handpiece, and in such alternative the suction tip may define a bend or angle, as discussed above with respect to bend 22.

Figure 6:
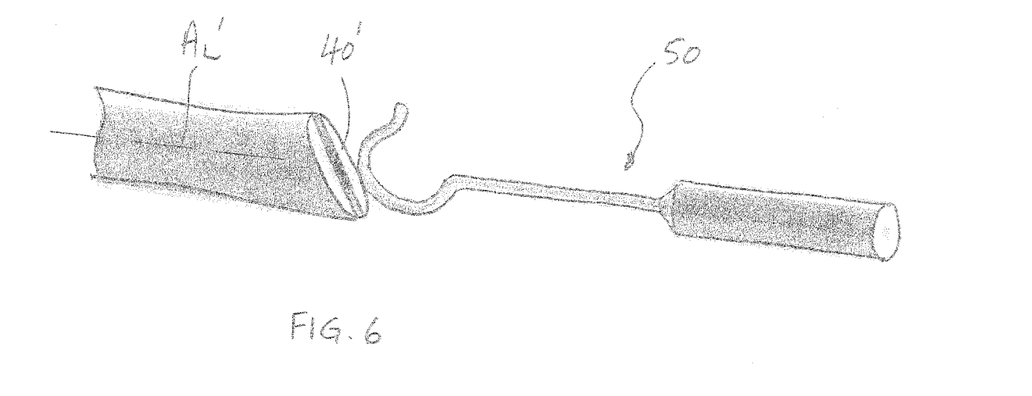
FIG. 6 is a view similar to FIG. 3, in which the distal face of the suction tip has an end surface provided at an oblique angle relative a longitudinal axis of the suction tip.

Referring to FIGS. 2 through 5, the distal portion 36 of the suction tip 30 is stepped down to a reduced outer diameter relative to the proximal portion 34 to facilitate insertion through the surgical opening and into the middle ear, to permit access through the middle ear structures, to provide the small scale suitable for engagement with a ossicular prosthesis, and to permit unobstructed visualization of the surgical site during use. The distal end 38 of the distal portion 36 is flattened out-of-round to form the distal opening 42 of passageway 32 into a non-circular slot. As such, perpendicular measurements perpendicular to the axis $A_L$ across the distal opening 42 of the passageway 32 define a length 44 and width 46 thereof. The distal end 38 of the distal portion 36 has an end face 40 oriented perpendicular to the longitudinal axis $A_L$ (FIG. 3) or an end face 40' oriented at an oblique angle relative to the longitudinal axis $A_{L'}$ (FIG. 6). An end face 40' at an oblique angle can facilitate delivery of the prosthesis 50 to middle ear structure such as the incus.

In accord with one embodiment of the suction tip 30, the suction tip is designed to engage a stapedial prosthesis 50 that replaces the stapes between another ossicle (the incus or malleus) and the stapes footplate. The stapedial prosthesis 50 has a partial or full loop 52 (also referred to as a crook) for extending about and engagement with an ossicle. The loop 52 is formed by a wire 54 of a diameter, and in one embodiment the wire has a diameter of 0.006 inch. Alternatively, the loop 52 may be formed of a flatter ribbon construction, in which case the larger transverse dimension of the ribbon construct is considered the diameter for purposes herein. The loop preferably extends in a plane and defines a loop diameter 54 with a center 56 and is sized to stably engage about the ossicle. The loop 52 extends into a shaft 58 with an axis 60. A supporting shoe 62 for placement on the stapes footplate is provided at the distal end of the shaft 58 in alignment with the axis 60.

For engagement with the stapedial prosthesis, the distal opening 42 of the suction tip 30 is specifically adapted to stably engage the loop 52 of the prosthesis 50. The width of the opening 42 is preferably sized to be slightly larger than the diameter of the wire 54, and the length of the opening 42 is adapted to receive therein a relatively small arc of the circumference of the loop 52; that is a portion of the loop extending through an angle α (e.g., preferably between 30° and 90° about the circumference of the loop) enters slightly inside the opening 42 when the length of the opening and the diameter of the loop 52 extend in a common plane. (FIGS. 4 and 5) In one embodiment for a loop 52 defined of 0.006 inch wire, the width 46 of the opening 42 is 0.002 inch larger in width than the wire diameter, i.e., the slot 42 has an opening width of 0.008 inch, to permit air to be drawn in around the wire 54 and into the opening 42 and through the passageway 32; thus, in such exemplar embodiment the opening width is one-third larger than the wire diameter. Other relative dimensions are possible, particularly for prostheses having different wire diameters; however opening sizes within 0.001-0.004 inch of the wire diameter shall be considered to be slightly larger while also being approximate in dimension for purposes herein. A notch 64 extends across the end face 40, in alignment with the length 44 of the slot opening 42. The notch 64 is preferably at a depth less than or equal to the diameter of the wire 54 of the loop 52, more preferably at a depth corresponding to greater than or equal to one-half the diameter of the wire, and in one embodiment for a loop defined of 0.006 inch wire the notch has a depth of 0.003 inch. The notch 64 defines a three-dimensional geometrical interface at the distal end 38 for contacting the loop 52, preferably in the form of symmetrical fixed stabilizing arms 66, 68 extending along opposing lengthwise sides of the slot opening 42.

Figure 2:
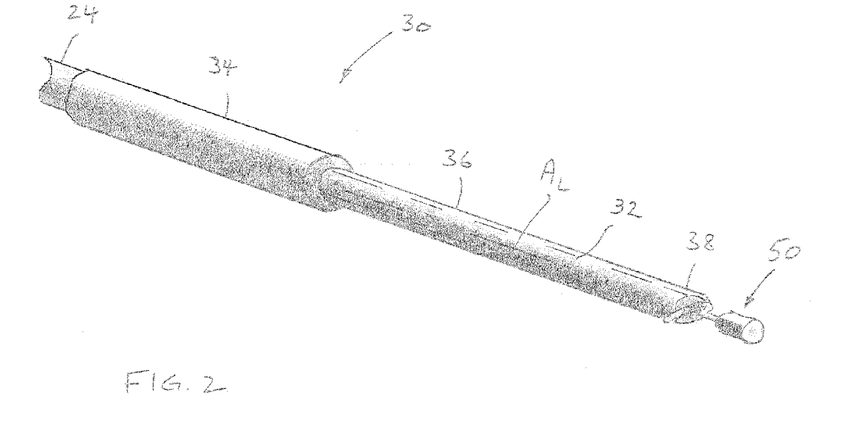
FIG. 2 is a perspective view of a first embodiment of the suction tip of the invention.

Referring back to FIG. 1, in use, the prosthesis-adapted suction tip 30 is coupled to the handpiece 12. The vacuum source 14 is operated. Suction is activated/deactivated through the handpiece by positioning the surgeon's thumb across the bypass hole on the thumbplate 19. When the thumb occludes the suction bypass hole, the suction tip is active. When the thumb is removed from the bypass hole the suction tip is deactivated. Alternately, a remote suction valve (operated via the footswitch 16 or a hand switch) may be used and activated by the surgeon or an assistant. Referring to FIG. 2, the distal end 38 of the suction tip 30 is then brought toward the loop 52 of the prosthesis 50. The applied suction draws the loop 52 in juxtaposition to the arms 66, 68 defined by the notch 64 and slightly inside the slot opening 42 and thereby picks up and couples the prosthesis to the tip. As the loop 52 is drawn therein, the prosthesis 50 is automatically properly oriented, being urged to reside within a plane angled in a predetermined relationship relative to the longitudinal axis of the suction tip; that is, the plane of the loop extends parallel with the lengthwise dimension of the slot opening 42. The width 46 of the slot opening 42 is slightly larger than the diameter of the wire 54 forming the loop, such that air is drawn in around the wire 54 and retains the prosthesis at the distal end 38 of the suction tip 30. In addition, the short arms 66, 68 defined by the notch 64 extend about the loop 52 and provide stability to the orientation of the loop and thus the prosthesis 50 in the plane P. Once the prosthesis is engaged in an orientation, the prosthesis-adapted suction tip 30 can be rotated on the handpiece about its longitudinal axis as shown at 70 (FIG. 3) to change its orientation about its longitudinal axis $A_L$. In the event the prosthesis 50 is contacted during implantation, the force of the suction draws the loop 52 of the prosthesis back into the slot opening 42 and the notch arms 66, 68 right the prosthesis into axial alignment with the suction tip 30. In addition, the prosthesis can be rotated about a center 56 of the loop without loosening the engagement of the tube adapter relative to the prosthesis, requiring any configuration of the tube adapter, and maintaining the same stability, all to permit a desirable angular positioning of the prosthesis during implantation.

Figure 7:
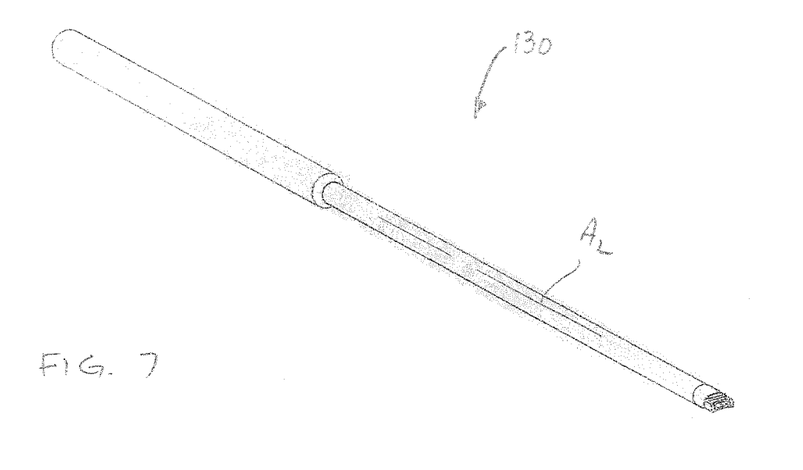
FIG. 7 is a perspective view of a suction tip according to a second embodiment of the invention.
Figure 8:
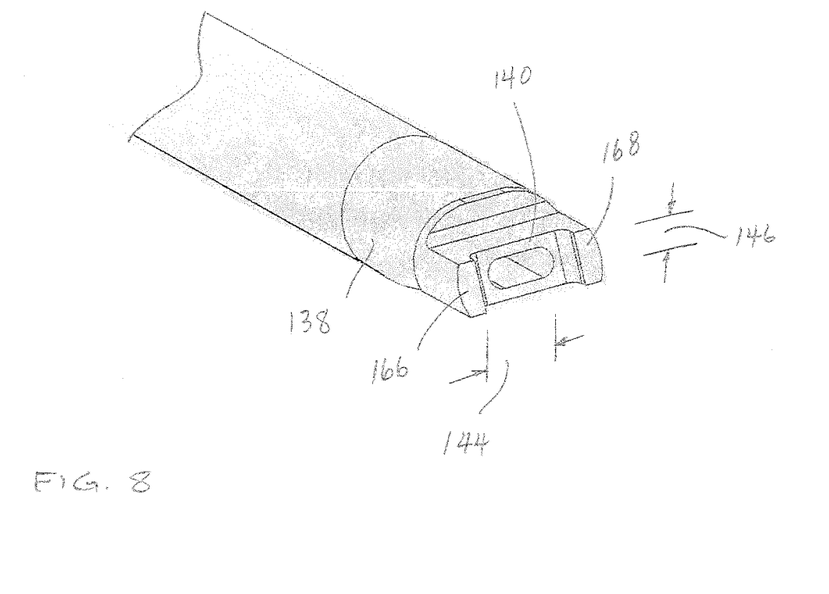
FIG. 8 is an enlarged perspective view of the distal end of the suction tip of FIG. 7.
Figure 9:
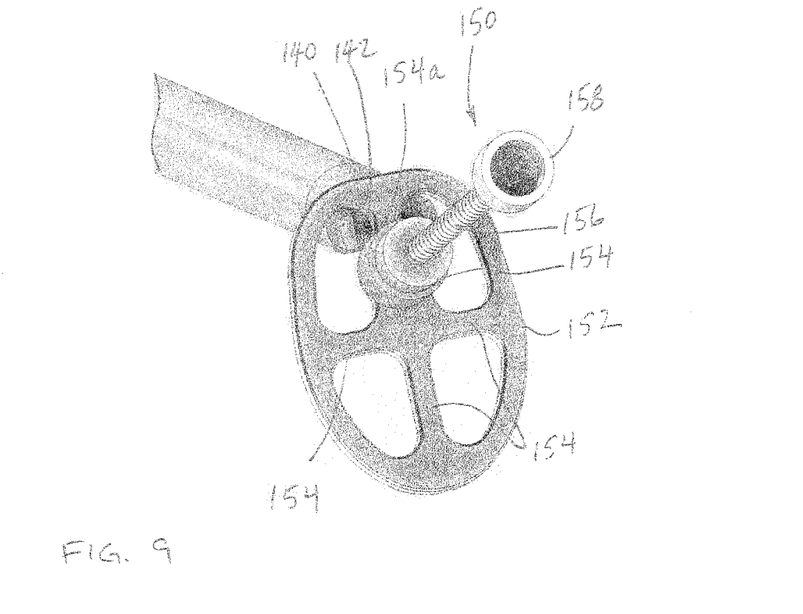
FIG. 9 is a perspective view of the distal end of the suction tip of FIG. 8 shown engaged relative to a partial ossicular prosthesis (PORP).

Turning now to FIGS. 7 through 9, a second prosthesis-adapted suction tip 130 is shown. The suction tip 130 is substantially similar to suction tip 30, described above, being an elongate tubular member having a longitudinal axis $A_L$, a passageway 132 extending along the axis, a proximal portion 134, and a distal portion 136. The proximal portion 134 is adapted to engage the distal end of the coupling portion 24 of the handpiece 12 of the suction system 10 (FIG. 1). The distal end of the distal portion 136 is structurally adapted for engagement relative to a portion of a head a total or partial ossicular prosthesis (TORP or PORP). More particularly, referring now to FIGS. 9 and 10, the head 152 of the shown adjustable PORP 150 has a disc-like configuration with generally radially extending flat spokes 154, each with a length and a width. The head 152 of the PORP also includes a collar 160, preferably fixed to one of the spokes 154*a*. The PORP includes a shaft 156 with a cup 158 at its distal end for attachment over the capitulum of the stapes. The shaft 156 is longitudinally displaceable relative to the collar 160 to effect a length change between the head and distal cup 158 (with the exposed portion of the shaft extending through the head being removable by the surgeon prior to implantation).

The suction tip 130 has a distal end 138 defining an end face 140 extending transverse to the longitudinal axis. The end face 140 is either perpendicular to the longitudinal axis or more preferably provided at an oblique axis thereto, as shown. A non-circular slot opening 142 is defined at the distal end of the distal portion. The slot opening has a longer length 144 and a shorter width 146, with the length 144 approximating but preferably slightly larger than the width of spoke 154*a* of the head 152 of the prosthesis 150. By way of example only, the spoke 154 has a width of 0.010 inch, and the slot has a length of 0.030 inch. The distal portion 136 of the suction tip has a three-dimensional geometric interface defined by two longitudinally extending fixed stabilizing arms 166, 168, one at either end of the elongate slot 152, between which the spoke 154*a* of the prosthesis head 152 can be stably received on the end face 140. By way of example, the arms have a length between 0.005-0.010 inch, sufficient to extend at least partially about the thickness of the spoke 154*a*, but not interfere with the collar 160. This structure is in distinction from the notch 64; arms 166, 168 are on opposite side of the lengthwise dimension of the slot opening 142, whereas arms

Figure 3:
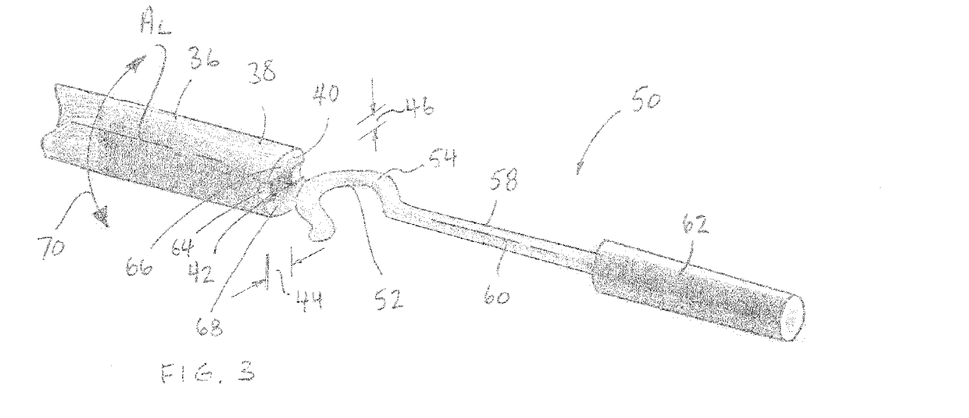
FIG. 3 is a perspective view of the suction tip of FIG. 2 in association with a stapedial prosthesis.
Figure 4:
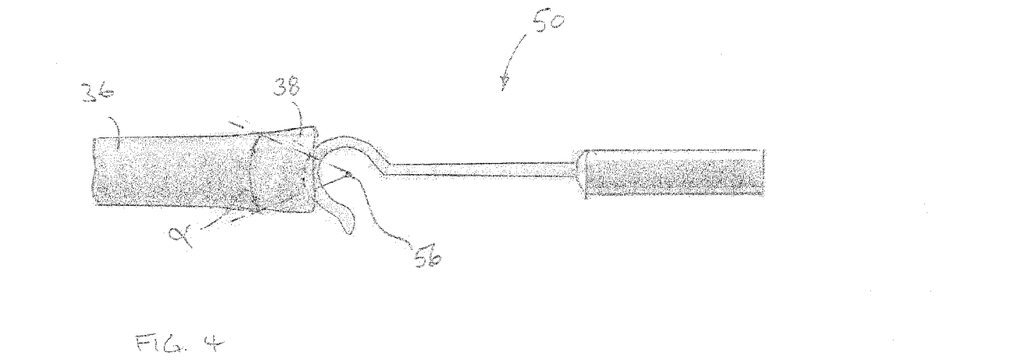
FIG. 4 is a top view of the suction tip of FIG. 2 shown engaged relative to a stapedial prosthesis.
Figure 5:
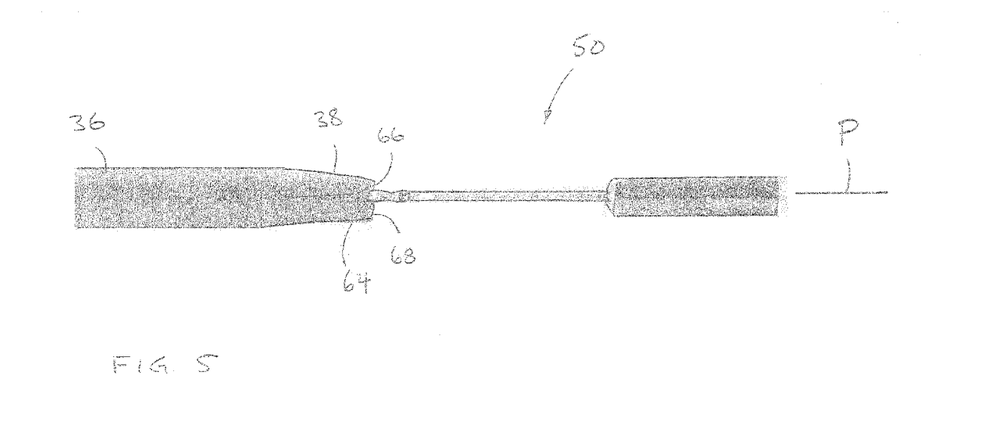
FIG. 5 is a side elevation view of the suction tip of FIG. 2 shown engaged relative to a stapedial prosthesis.

66, 68 are on opposite sides of the widthwise dimension of the opening 42 (FIG. 3). It is also appreciated that other three-dimensional geometrical interfaces can be provided at the distal end 138 for contacting a proximal portion of the implant. For example, referring to FIG. 11, the distal end 138' can be formed with one or more pegs, such as three round pegs 166', 168', 170' that provide a sufficient three-dimensional interface for orientation, support, and stabilization of an implant thereat. Also, with a given three dimensional interface, the distal opening 142' may be round, in distinction from slot-shaped. Referring back to FIGS. 9 and 10, when spoke 154a is against the end face 140, the head 152 is retained in a plane at a defined angle relative to the longitudinal axis (i.e., orthogonal to the end face 140), and the shaft 156 is retained to extend along a defined axis.

Figure 10:
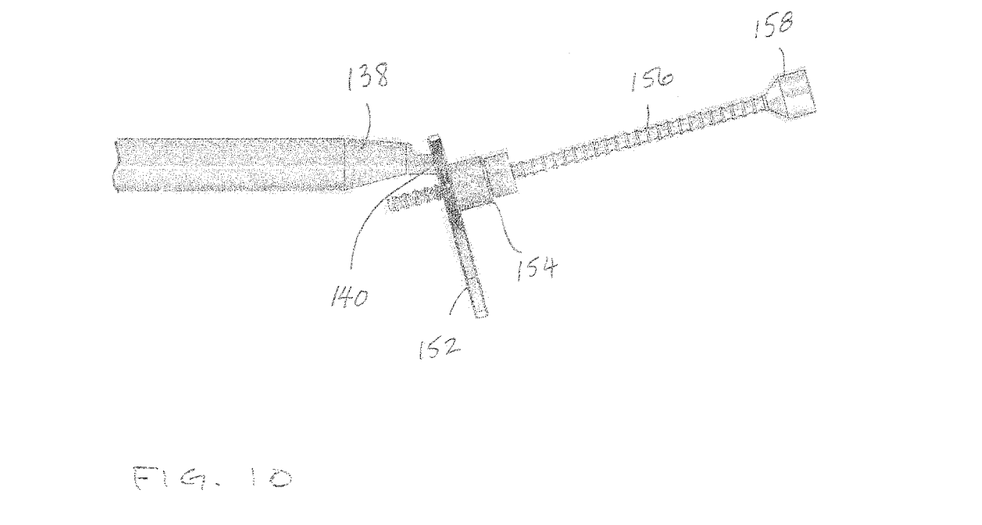
FIG. 10 is a side elevation view of the distal end of the suction tip of FIG. 8 shown engaged relative to a partial ossicular prosthesis (PORP).
Figure 11:
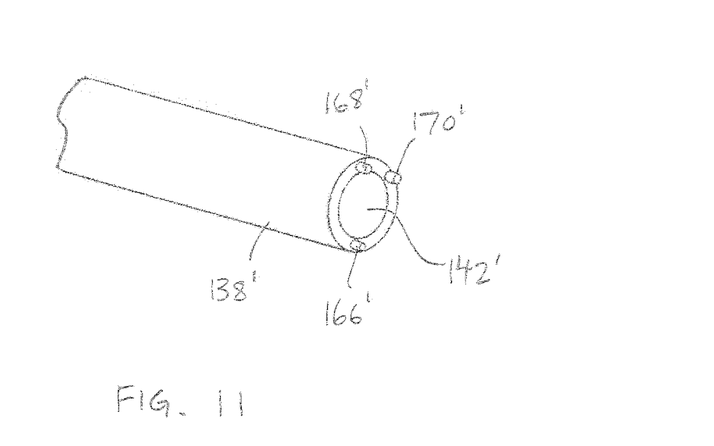
FIG. 11 is a broken perspective view of an alternate configuration of the distal end of a suction tip according to the invention.

In use, suction is applied through the handpiece 12 and suction tip 130. The distal end 136 of the suction tip 130 is then brought toward spoke 154a of the head of the prosthesis, and the suction draws the spoke against the distal face 140. The flat spoke is held flat against the distal face 140, with air being drawn around the widthwise edges of the spoke 154a at the outer ends of the elongate slot. The arms 166, 168 guide the prosthesis onto the suction tip, provide stability in orientation, and provide retention from inadvertent movement off the suction tip. The orientation of the end face 140 orients the prosthesis 150 relative to the longitudinal axis $A_L$ to provide an approach angle into the middle ear that facilitates implantation. The suction tip 130 can be rotated on the coupling portion 22 of the handpiece 12 (FIG. 1) to change its rotational orientation about its longitudinal axis. In the event the prosthesis is contacted during implantation, the suction tip is adapted to re-orient the prosthesis into the intended orientation, drawing the spoke 154a of the head 152 of the prosthesis back between the arms 166, 168 and against the end face 140, into the desired alignment.

In either embodiment, the prosthesis may be released without potentially disrupting (via transmitted vibration) mechanical activation at the handpiece. Once the prosthesis is placed at its intended location, suction is deactivated via the footswitch 16 and the prosthesis is thereby released from the suction tip 30, 130.

The disclosed suction tips are easier to manufacture than mechanical graspers, are significantly less expansive to manufacture than mechanically operated graspers, and provides more stability and control than any existing instruments for manipulating very small implants such as ossicular prostheses for accurate implantation. In addition, the suction tip provides for self-correction, causing a prosthesis to re-orient into the prior intended configuration in the event the prosthesis is unintentionally dislodged from its initial configuration.

As variations in implant design may require variations in the suction tip geometry for the specific geometry of the implant, it is contemplated that an implant and a customized suction tip therefore may be packaged together and provided to the surgeon as a kit, in sterile packaging.

There have been described and illustrated herein embodiments of a suction system and suction tip therefore for the implantation of an ossicular prosthesis, and method of implanting an ossicular prosthesis using such system and device. While particular embodiments of the invention have been described, it is not intended that the invention be limited thereto, as it is intended that the invention be as broad in scope as the art will allow and that the specification be read likewise. Thus, while several preferred dimensions have been described, it is not intended that the invention be limited to such dimensions. Also, while the invention has been described with respect to two exemplar ossicular prostheses, it is not intended that its application be so limited; the system described herein is intended for and if necessary can be readily adapted in dimension, slot opening, arm size, face angle, etc., to accommodate a wide variety of currently available and future existing ossicular prostheses. Moreover, it is appreciated that the system of the invention is applicable to other implants for the middle ear, including active and passive hearing devices. Further, while certain materials have been specified, the invention is not limited thereto. It will therefore be appreciated by those skilled in the art that yet other modifications could be made to the provided invention without deviating from its spirit and scope as claimed.

What is claimed is:

1. A suction tip system, comprising:
   a) a middle ear implant having a proximal end;
   b) a suction tip defining a longitudinal axis, a passageway, a proximal portion and a distal portion, said proximal portion adapted for coupling with the distal end of the suction handpiece, and said distal portion having a distal end defining an opening into the passageway and a three dimensional geometric interface for said implant; and
   c) a suction handpiece couplable to a vacuum source, said proximal portion of said suction tip coupled to said suction handpiece, and said suction handpiece adapted to provide fluid communication from the vacuum source to said passageway of said suction tip,
   wherein when suction is applied from the suction handpiece through said passageway of said suction tip and when said distal end of said suction tip and said proximal end of said implant are provided in proximity, a portion of said proximal end of said implant is drawn and held against said distal end in juxtaposition to said at least one fixed stabilizing member such that said three-dimensional geometric interface supports and orients said implant in a desired orientation.

2. A system according to claim 1, wherein:
   said suction tip has a longitudinal axis and a distal end face, and said end face is oriented at an oblique angle relative to said longitudinal axis.

3. A suction tip system for use with a suction handpiece having a distal end, comprising:
   a) a middle ear implant having a proximal end; and
   b) a suction tip defining a longitudinal axis, a passageway, a proximal portion and a distal portion, said proximal portion adapted for coupling with the distal end of the suction handpiece, and said distal portion having a distal end defining an opening into the passageway, and said opening is a non-circular, elongate slot-like opening with a length and width, each of said length and width extending transverse to said longitudinal axis, and said distal end defining a three dimensional geometric interface for said implant,
   wherein when suction is applied from the suction handpiece through said passageway of said suction tip and when said distal end of said suction tip and said proximal end of said implant are provided in proximity, a portion of said proximal end of said implant is drawn and held against said distal end in juxtaposition to said three-dimensional geometric interface such that said three dimensional geometric interface supports and orients said implant in a desired orientation.

4. A system according to claim 3, wherein:
   said geometric interface includes stabilizing members defined on opposite sides of said opening.

5. A system according to claim 4, wherein:
   said stabilizing members are defined on said opposite sides across said width of said slot.

6. A system according to claim 5, wherein:
said stabilizing member are defined by a notch in said distal end of said suction tip, said notch extending in alignment with said length of said slot.

7. A system according to claim 4, wherein:
said stabilizing member are defined on said opposite sides across said length of said slot.

8. A system according to claim 1, wherein:
said implant is a stapedial prosthesis having a proximal loop and distal end for placement at a stapes footplate.

9. A system according to claim 4, wherein:
said implant is a stapedial prosthesis having a proximal loop for engagement with one of a malleus and an incus, and distal end for placement at a stapes footplate, and said loop is constructed of a material having a diameter, and said width of said slot-like opening and said loop material diameter are similar in dimension.

10. A system according to claim 9, wherein:
said width is greater than said material diameter by no more than 0.004 inch.

11. A system according to claim 9, wherein:
said loop of said prosthesis extends within a plane and defines a center, and
when suction is applied to draw said prosthesis against said distal end and in juxtaposition to said stabilizing members, said prosthesis is urged into an orientation in which said longitudinal axis extends through said plane.

12. A system according to claim 11, wherein:
when said prosthesis is urged in the orientation in which said longitudinal axis extends through said plane, said prosthesis can be rotated about said center of said loop while retained against said distal end of said suction tip.

13. A system according to claim 4, wherein:
said implant is a prosthesis having a proximal disc-like head with a spoke, a distal portion, and a shaft extending therebetween, said spoke having a width, said stabilizing members spaced apart to receive said spoke.

14. A system according to claim 13, wherein:
said length of said opening is greater than said width of said spoke.

15. A suction tip system for use with a suction handpiece having a distal end, comprising:
 a) an otologic prosthesis having a proximal end; and
 b) a suction tip having a longitudinal axis, a passageway, a proximal portion and a distal portion, said proximal portion adapted for coupling with the distal end of the suction handpiece, and said distal portion having a distal end defining an opening into the passageway, and a distal end face oriented at an oblique angle relative to said longitudinal axis, and a three dimensional geometric interface for said implant,
 said three-dimensional geometric interface configured to support and orient said prosthesis in a desired orientation when said distal end of said suction tip and said proximal end of said otologic prosthesis are provided in proximity and suction is applied from the suction handpiece through said passageway of said suction tip to said otologic prosthesis.

16. A suction tip system according to claim 15, wherein the otologic prosthesis is a stapedial prosthesis.

17. A suction tip system according to claim 16, wherein the proximal end of the stapedial prosthesis is in the form of a loop of wire.

\* \* \* \* \*